US012023466B2

(12) United States Patent
Alexander

(10) Patent No.: US 12,023,466 B2
(45) Date of Patent: Jul. 2, 2024

(54) SYSTEMS AND METHODS FOR IMPROVING FLUID FLOW DURING MEDICATION DELIVERY PROCEDURES

(71) Applicant: Damea Alexander, Marysville, OH (US)

(72) Inventor: Damea Alexander, Marysville, OH (US)

( * ) Notice: Subject to any disclaimer, the term of this patent is extended or adjusted under 35 U.S.C. 154(b) by 336 days.

(21) Appl. No.: 17/093,778

(22) Filed: Nov. 10, 2020

(65) Prior Publication Data

US 2022/0143312 A1 May 12, 2022

(51) Int. Cl.
| | |
|---|---|
| *A61M 5/168* | (2006.01) |
| *A61M 5/165* | (2006.01) |
| *A61M 39/10* | (2006.01) |
| *A61M 39/28* | (2006.01) |
| *A61M 5/14* | (2006.01) |
| *A61M 39/00* | (2006.01) |

(52) U.S. Cl.
CPC ........ *A61M 5/16881* (2013.01); *A61M 5/165* (2013.01); *A61M 39/10* (2013.01); *A61M 39/28* (2013.01); *A61M 5/1411* (2013.01); *A61M 2039/0081* (2013.01)

(58) Field of Classification Search
CPC .......... A61J 1/20; A61J 1/2003; A61J 1/2006; A61J 1/201; A61J 1/2068; A61J 1/2072; A61J 1/2075; A61J 1/2096; A61J 1/2082; A61M 5/162; A61M 5/1626; A61M 5/1782; A61M 2005/1623
See application file for complete search history.

(56) References Cited

U.S. PATENT DOCUMENTS

| 2,208,550 | A | * | 7/1940 | Shapiro | ................. | A61M 5/162 |
| | | | | | | 604/405 |
| 2,409,343 | A | * | 10/1946 | Curtis | ................... | A61M 5/162 |
| | | | | | | 604/411 |
| 2,562,445 | A | | 7/1951 | Butler | | |
| 2,770,234 | A | * | 11/1956 | Nesset | ................. | A61M 5/162 |
| | | | | | | 215/261 |
| 2,777,443 | A | * | 1/1957 | Thomas | .............. | A61M 5/1626 |
| | | | | | | 604/257 |
| 2,817,372 | A | * | 12/1957 | Barr, Jr. | ................ | A61M 5/162 |
| | | | | | | 604/257 |

(Continued)

FOREIGN PATENT DOCUMENTS

WO 2019/079335 A1 4/2019

*Primary Examiner* — Kami A Bosworth
(74) *Attorney, Agent, or Firm* — Standley Law Group LLP; Adam J. Smith; Kenny W. Pung

(57) ABSTRACT

Systems and method for improving fluid flow during medication delivery procedures, such as infusions or pooling, are provided. A spike is punctured though a seal in a container. A liquid substance is drained from said container through a pathway in the spike. In some embodiments, the spike includes a channel which permit sliding movement of a snorkel for elevation above a fluid line of the liquid substance to permit air to enter the container from outside without foaming the liquid substance. Alternatively, the snorkel is punctured through the seal adjacent to the spike. Alternatively, or in addition, an airflow control device is provided at the container at a location above an anticipated fluid line of the liquid substance when the container is positioned for delivery of the liquid substance.

12 Claims, 8 Drawing Sheets

(56) References Cited

U.S. PATENT DOCUMENTS

| | | | | |
|---|---|---|---|---|
| 2,847,995 | A | * | 8/1958 | Adams .................. A61M 5/162 604/905 |
| 3,316,908 | A | * | 5/1967 | Burke .................. A61M 5/1626 55/482 |
| 3,456,647 | A | | 7/1969 | Wada |
| 4,532,969 | A | * | 8/1985 | Kwaan .................. A61J 1/2096 141/285 |
| 4,857,068 | A | | 8/1989 | Kahn |
| 6,609,520 | B1 | | 8/2003 | Carlsen et al. |
| 2008/0269680 | A1 | | 10/2008 | Ibranyan et al. |
| 2008/0269713 | A1 | | 10/2008 | Kavazov |
| 2009/0159485 | A1 | | 6/2009 | Jakob et al. |
| 2012/0085784 | A1 | * | 4/2012 | Bakris .................. A61M 35/00 222/23 |
| 2012/0179129 | A1 | * | 7/2012 | Imai ...................... A61J 1/2096 604/414 |
| 2012/0289900 | A1 | * | 11/2012 | Chong .................. A61J 1/2096 604/113 |
| 2015/0320641 | A1 | | 11/2015 | Fangrow |
| 2018/0116909 | A1 | | 5/2018 | Sealfon et al. |

\* cited by examiner

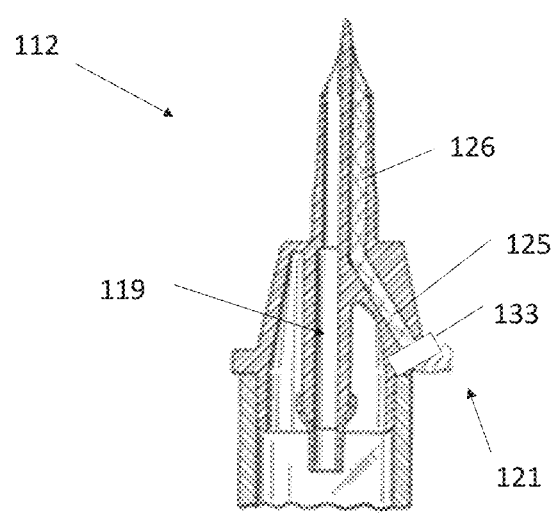
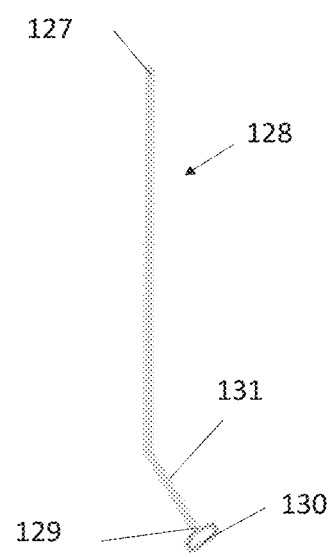
Figure 4
Figure 5

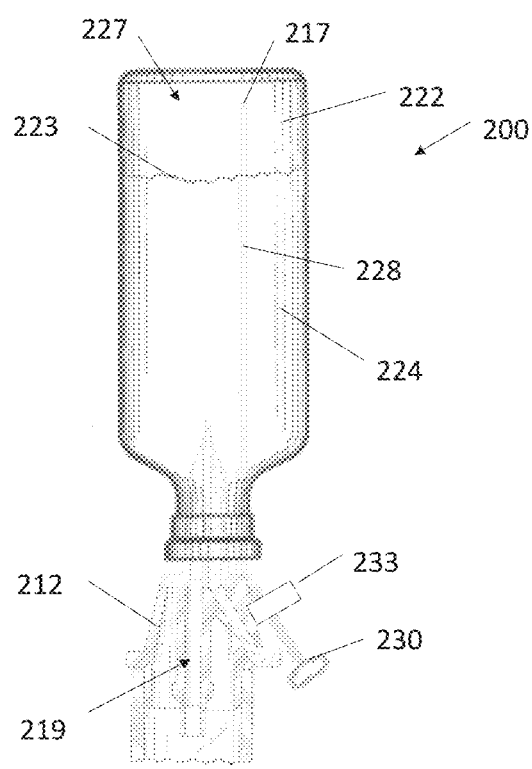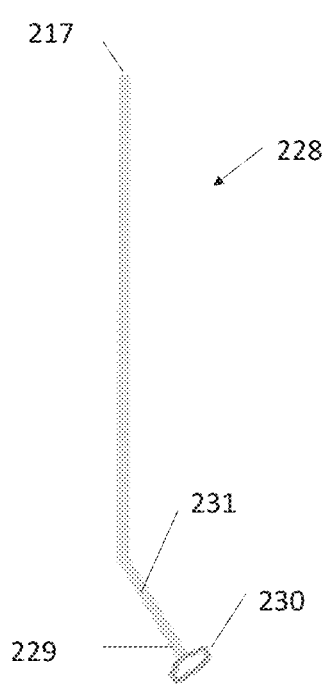
Figure 6A                    Figure 6B

```
┌─────────────────────────────┐
│ Close airflow control device │
└─────────────┬───────────────┘
              ▼
┌─────────────────────────────┐
│ Orient container for delivery│
└─────────────┬───────────────┘
              ▼
┌─────────────────────────────┐
│  Insert spike into container │
└─────────────┬───────────────┘
              ▼
┌─────────────────────────────┐
│  Open airflow control device │
└─────────────┬───────────────┘
              ▼
┌─────────────────────────────┐
│       Deliver substance      │
└─────────────────────────────┘
```

Figure 9

SYSTEMS AND METHODS FOR IMPROVING FLUID FLOW DURING MEDICATION DELIVERY PROCEDURES

CROSS-REFERENCE TO RELATED APPLICATIONS

This application makes no priority claim.

TECHNICAL FIELD

Exemplary embodiments relate generally to systems and methods for improving fluid flow during medication delivery procedures, such as infusions or pooling.

BACKGROUND AND SUMMARY OF THE INVENTION

Medication often needs to be delivered from one location to another for a variety of reasons. Examples of such procedures include, but are not limited to, infusions and pooling. Infusions or pooling are performed for a variety of medical reasons. Infusions may be performed as part of a treatment regimen for certain acute or chronic disease. For example, without limitation, certain autoimmune disorders may require periodic infusions of immunoglobulin, sometimes for the remainder of the patient's life. These medications after often expensive and may be difficult to obtain. Certain such infusions treatments may account for a significant amount of insurance expenditures. Traditionally, delivery systems are used which include a spike. The spike is inserted into a container. A pathway is provided through the spike for draining fluid from the container. Tubing fluidly connects the spike to an intravenous device inserted into a patient's vascular system such that the medication may be delivered to the patient.

In another similar procedure, pooling, medication is transferred from one container to another. Similar steps are generally followed, but the tubing is connected to a second container to which the medication is transferred. For example, medication may be transferred from a rigid container, such as a bottle, to a flexible one, such as a bag. This may be performed for preferences, to dilute medication, to combine medications or otherwise create solutions or other compounds, and/or to share the medication among multiple patients. Typically, the medications or other substances being infused or pooled are provided in liquid form. Such medications may likewise be expensive and are often difficult to obtain.

Traditional spikes may be vented or non-vented. Generally, vented spikes are not needed where the container is collapsible, such as with bags. However, vented spikes are generally required where the container is rigid, such as with glass or rigid plastic containers. Where vented spikes are used, the vent may be opened to permit outside air to enter the container, thereby allowing the substance in the container to drain for administration to the patient or transfer to another container. A valve may be provided at the vent to permit air to enter the container while preventing the substance from exiting. An example of a vented spike is provided in U.S. Pat. No. 4,857,068. The air ingested through the vent may rise through the substance in the container, generally causing the substance in the container to foam. The foamed substance cannot be readily delivered to the patient, and thus generally remains in the container after administration or transfer is ceased. This generally results in significant amounts of undelivered substance left remaining in the container which is never delivered to the patient. Therefore, what is needed are systems and methods for improving fluid flow during infusions or pooling.

Systems and methods are provided which improve fluid flow during medication delivery procedures, such as but not limited to, infusions and pooling. Such systems and methods may be designed to provide smooth draining from a container during such procedures, thereby reducing or eliminating foaming and increasing the amount of substances administered to the patient, transferred, or otherwise delivered. In exemplary embodiments, the spike may comprise a channel configured to accommodate a snorkel in a sliding manner. The snorkel may be inserted into the channel of the spike. A first, open end of the snorkel may be elevated above a fluid level of the substance within the container to permit air to enter the container during infusion, pooling, or the like to permit draining of the substance. Because the air may enter above the substance, without passing directly through it, foaming may be reduced or eliminated.

A protective cover may be provided from an entrance of the channel to a second, open end of the snorkel. The protective sleeve may be collapsible so that the snorkel may be selectively advanced into the container and retracted therefrom. This may permit the snorkel to be inserted and removed from the container while maintaining a sterile environment. In this way, the snorkel may be reused in multiple containers. For example, without limitation, this may permit multiple containers to be used during an infusion, pooling, or other procedure. For example, without limitation, this may permit utilization with different size containers. A valve, port, or the like may be provided on an end of, and/or along, the snorkel. In this way, the substance in the container may be prevented from exiting through the snorkel while being inserted through the substance.

The snorkel may snugly fit within the channel such that the snorkel may be temporarily secured at locations along the channel. Alternatively, or additionally, a clamp or other device may be used to secure the snorkel relative to the channel.

Alternatively, or additionally, the snorkel may be inserted through the seal of the container adjacent to the spike. The seal may be of sufficient size to accommodate both a portion of the spike and the snorkel. In such embodiments, the spike may include the pathway for draining the substance. The channel for the snorkel may not be required, and traditional vented or unvented spikes may be used. The seal and/or the snorkel may comprise one or more materials having sufficient frictional properties to permit the snorkel to be temporarily secured at various positioned relative to said seal. For example, without limitation, the seal may comprise a rubberized material and the snorkel may comprise a polymer, metal, or the like. A fluid control device may be provided on a second end of the snorkel. A first end of the snorkel may be blunted, though such is not required.

Alternatively, or additionally, an airflow control device may be provided at the container. The airflow control device may comprise a valve, such as but not limited to a one-way valve, port, or the like. The airflow control device may be positioned above the fluid line of the substance when the container is positioned for administration, transfer, or other dispensation. For example, without limitation, the airflow control device may be located on or near the bottom surface of the container.

Further features and advantages of the systems and methods disclosed herein, as well as the structure and operation of various aspects of the present disclosure, are described in detail below with reference to the accompanying figures.

BRIEF DESCRIPTION OF THE DRAWINGS

In addition to the features mentioned above, other aspects of the present invention will be readily apparent from the following descriptions of the drawings and exemplary embodiments, wherein like reference numerals across the several views refer to identical or equivalent features, and wherein:

FIG. 4 is a side sectional view of an exemplary spike of the delivery system of FIGS. 3A-3C, shown in isolation from other components of the delivery system;

FIG. 5 is a side view of the snorkel of the delivery system of FIGS. 3A-3C, shown in isolation from other components of the delivery system;

FIG. 6A is a side sectional view of another exemplary delivery system with improved fluid flow in accordance with the present invention;

FIG. 6B is a side view of the snorkel of the delivery system of FIG. 6A, shown in isolation from other components of the delivery system;

FIG. 9 is a flow chart for an exemplary method of using the delivery system of FIGS. 8A-8C in accordance with the present invention.

DETAILED DESCRIPTION OF EXEMPLARY EMBODIMENT(S)

Various embodiments of the present invention will now be described in detail with reference to the accompanying drawings. In the following description, specific details such as detailed configuration and components are merely provided to assist the overall understanding of these embodiments of the present invention. Therefore, it should be apparent to those skilled in the art that various changes and modifications of the embodiments described herein can be made without departing from the scope and spirit of the present invention. In addition, descriptions of well-known functions and constructions are omitted for clarity and conciseness.

Embodiments of the invention are described herein with reference to illustrations of idealized embodiments (and intermediate structures) of the invention. As such, variations from the shapes of the illustrations as a result, for example, of manufacturing techniques and/or tolerances, are to be expected. Thus, embodiments of the invention should not be construed as limited to the particular shapes of regions illustrated herein but are to include deviations in shapes that result, for example, from manufacturing.

Figure 1:
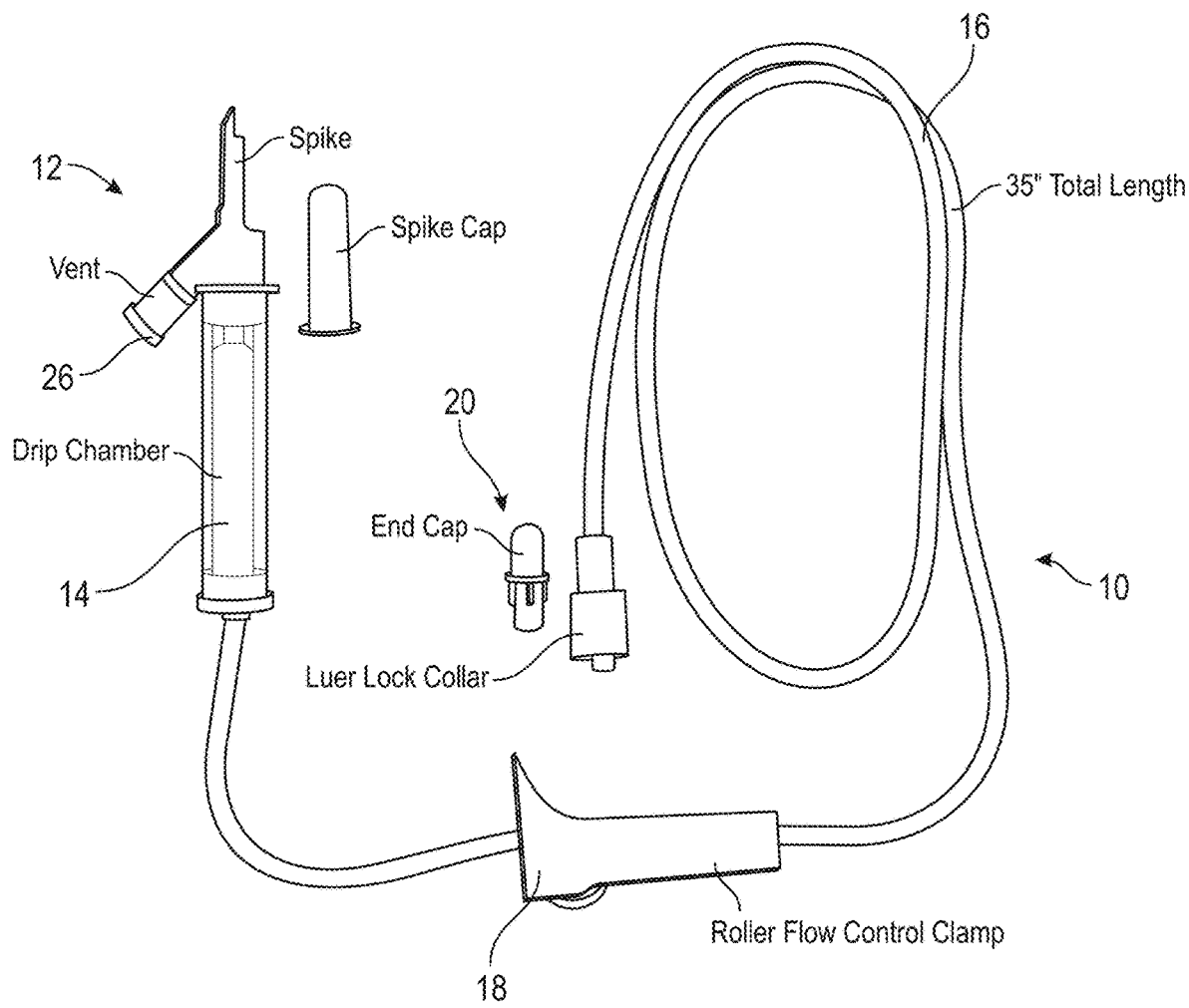
FIG. 1 is a plan view of a traditional delivery system.

FIG. 1 illustrates a traditional delivery system 10. The delivery system 10 may be used for various medication delivery procedures, such as but not limited to, infusions and pooling. The traditional delivery system 10 may include a spike 12 connected to a drip chamber 14. The drip chamber 14 may be connected to a first end of tubing 16. A flow control device 18 may be provided along the tubing 16. One or more adapters or devices 20 may be connected to a second end of the tubing 16 for providing, or connecting to devices which provide, access to a patient's vascular system, such as but not limited to needles, ports, or the like. The spike 12 may comprise a vent 26, or may be ventless.

Figure 2A:
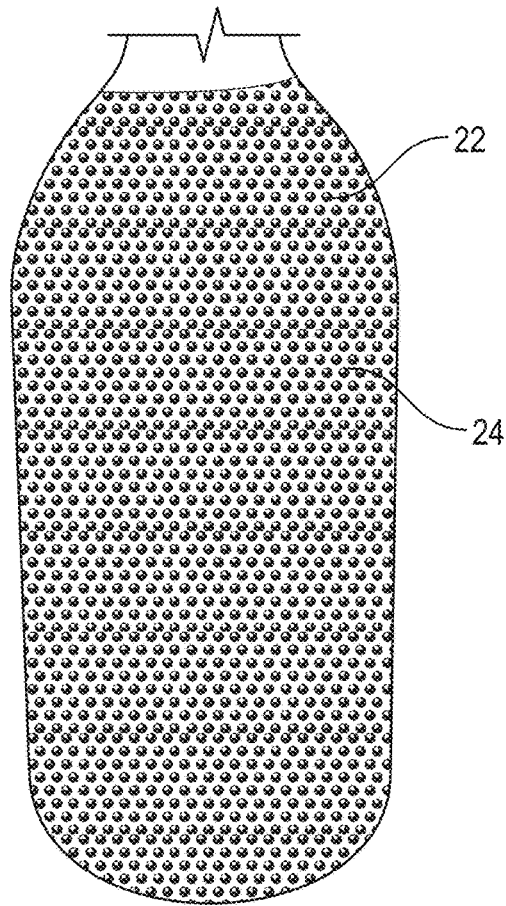
FIG. 2A is a front view of an exemplary container illustrating an exemplary substance after administration or transfer using the traditional delivery system of FIG. 1.

FIG. 2A illustrates an exemplary container 22 with a foamed substance 24 after administration or transfer using the traditional delivery system 10. The spike 12 may be used to puncture a seal provided on the container 22. The container 22 may be inverted to allow the substance 24 to be administered or transferred, at least in part, by gravitational forces. The vent 26 on the spike 12, if provided, may be left closed when the container 22 is punctured by the spike 12. The drip chamber 14 may be squeezed to begin the flow of the liquid substance 24 while the vent 26 remains closed. The vent 26 may subsequently be opened to permit air to enter the container 22 so that the liquid substance 24 may be slowly drained from the contained 22 for administration to the patient, transfer to another container, or other delivery. The vent 26 may incorporate a valve or cap for controlling air flow. For example, the vent 26 may be configured to allow airflow into the container 22 while preventing the substance 24 from existing the container through the vent 26. Because the vent 26 is located below a fluid line of the substance 24, the air entering the container 22 may be forced to bubble up through the liquid substance 24, which may result in the illustrated foaming shown in FIG. 2A. The spike 12 may not be configured to accept the foamed substance 24, and thus the foamed substance 24 is typically left un-administered to the patient, un-transferred to another container 22, or otherwise undelivered to a desired location.

Figure 2B:
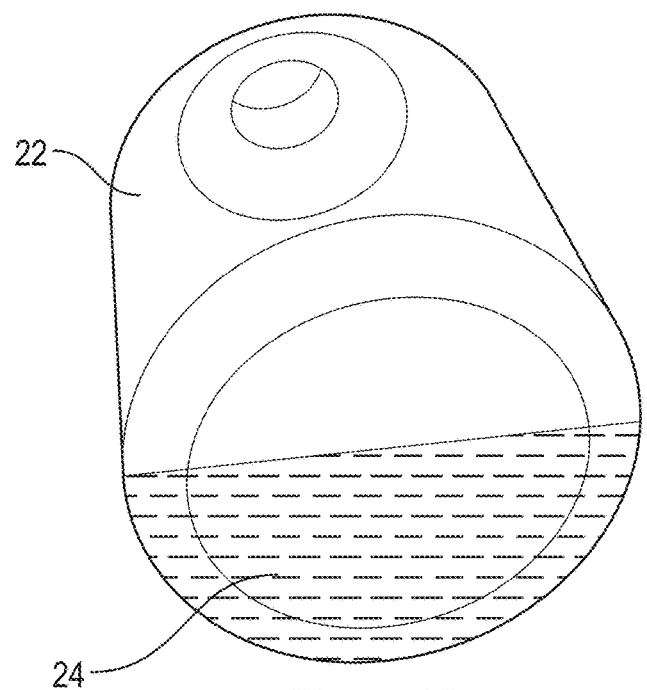
FIG. 2B is a bottom view of the container of FIG. 2A after the foamed substance is allowed to condense.

FIG. 2B illustrates the foamed substance 24 being allowed to condense back down to a liquid. FIG. 2B provides an example of the amount of substance 24 which may be left in the container 22, un-administered to the patient, un-transferred, or otherwise un-removed. It may take a significant amount of time, up to several hours for example, for the foamed substance 24 to re-condense. As such, this leftover substance 24 is typically discarded.

Figure 3A:
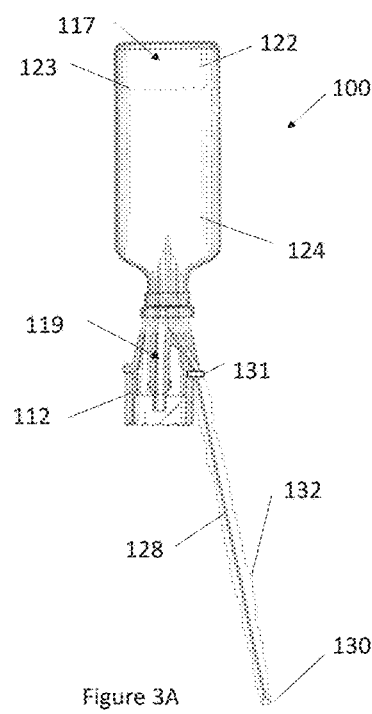
FIG. 3A is a side sectional view of an exemplary delivery system with improved fluid flow in accordance with the present invention.
Figure 3B:
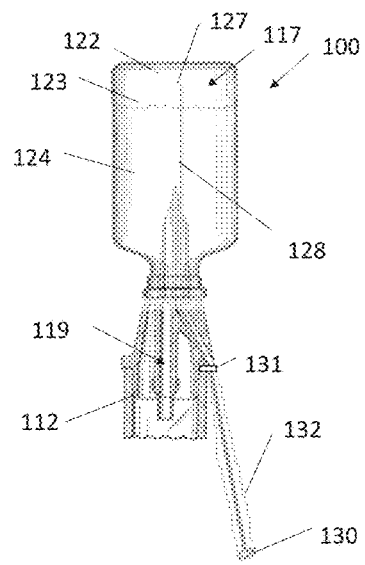
FIG. 3B is a side sectional view of the delivery system of FIG. 3A with a snorkel partially inserted, such as for use with a relatively small container.
Figure 3C:
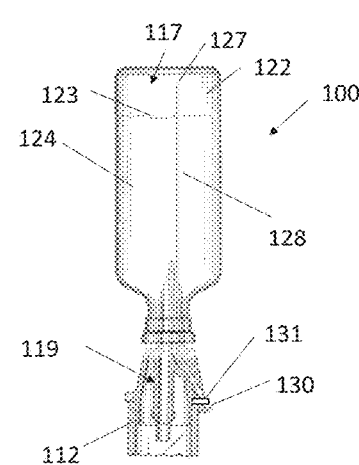
FIG. 3C is a side sectional view of the delivery system of FIG. 3A with the snorkel fully inserted, such as for use with a relatively large container.

FIG. 3A through FIG. 3C illustrate an exemplary medication delivery system with improved fluid flow 100 (hereinafter also the "system 100"). Similar items may be numbered similarly but increased by 100 (e.g., 12 to 112). Any type or kind of container 122 may be utilized.

The system 100 may be used to delivery any type or kind of substance 124, which is typically provided as a liquid. The substance 124 may comprise any number and type of ingredients. The substance 124 may be provided as a solution, such as a colloid solution, compound, or the like. Typically, at least one medication and at least one inactive carrying fluid are provided in the substance 124, though such is not required. Any type or kind of inactive ingredient, or combination of inactive ingredients, may be utilized. Any type or kind of medication, or combination of medications, may be utilized. The medications may comprise one or more naturally occurring substances, synthesized substances, combinations thereof, or the like. For example, at least one of the medications may comprise one or more proteins or immunoglobulin, such as but not limited to, albumin. These substances may be expensive and/or difficult to obtain. In the example of Immunoglobulin, which is provided without limitation, a single container 122 which is typically administered to a single patient, may be derived from plasma donations from multiple individuals. With the scarcity of available plasma donations, it is readily apparent why discarding even relatively small amounts of remaining substance 124 is undesirable.

In exemplary embodiments, the container 122 may comprise a bottle or otherwise rigid or semi-rigid container. The container 122 may comprise glass, plastic, or the like. The container 122 may comprise a puncturable seal at an otherwise open end for receiving a spike 112. In other exemplary embodiments, the container 122 may be flexible, such as but not limited to, where the container 122 comprise a bag. Even in the case of such flexible containers, certain amounts of substance 124 may remain in the container 122, such as within creases or air pockets created during administration, transfer, or other delivery. Thus, use of the delivery system 100 may also provide advantages when used with such flexible containers 122.

The spike 112 may comprise one or more pathways 119 for draining the substance 124 from the container 122.

As illustrated particularly in FIG. 4, the spike 112 may comprise a channel 126. The channel 126 may provide a pathway through the spike 112 between the container 122 and the ambient environment when said spike 112 is inserted into the container 122, such as by puncturing the seal.

The channel 126 may be configured to accommodate a snorkel 128. The channel 126 may comprise one or more non-linear section 125, such as but not limited to angular sections, curves, sinuous passages, or the like, though such is not required. For example, in other exemplary embodiments, the channel 126 may extend in an entirely straight line through the spike 112. The snorkel 128 may comprise one or more sufficiently flexible materials to negotiate the non-linear section 125 of the channel 126. Alternatively, or additionally, the snorkel 128 may comprise one or more sufficiently rigid material to remain stiff and upright when inserted into the container 122. The snorkel 128 may comprise a polymer, metal, combinations thereof, or the like. Some or all of the snorkel 128 may be hollow to facilitate the flow of fluids, such as but not limited to air, through the snorkel 128.

The snorkel 128 may be configured for sliding movement within the channel 126. The snorkel 128 may be moveable between a retracted position (see e.g., FIG. 3A), to an extended position (see e.g., FIG. 3C), or be secured at a position between such extended and retracted positions (see e.g., FIG. 3B). The snorkel 128 and/or the spike 112, or components thereof, may be configured to permit the snorkel 128 to be temporarily secured at the retracted position, the extended position, and/or positions therebetween. In exemplary embodiments, the fit between the snorkel 128 and the channel 126 may be sufficiently snug to permit a press or friction fit that secure the position of the snorkel 128 relative to the spike 112. For example, without limitation, a force greater than a predetermined amount may be required to move the snorkel 128 through the channel 126.

In other exemplary embodiments, a securing device 133 may be provided at, or connected to, the spike 112. The securing device 133 may be configured to secure the position of the snorkel 128 relative to the channel 126. The securing device 133 may comprise a strap and/or clamp for compressing the snorkel 128, such as but not limited to a C-clamp, hose clamp, tubing clamp, utility clamp, some combination thereof, or the like. Any type of kind of securing device 133 may be utilized. In exemplary embodiments, the securing device 133 may be positioned at or near the entrance 121 of the channel 126, though any location may be utilized. For example, without limitation, the securing device 133 may be positioned along the channel 126. The securing device 133 may be normally secured, normally unsecured, or the like.

As illustrated particularly in FIG. 5, the snorkel 128 may comprise a hollow member. The snorkel 128 may comprise a first end 127 and a second end 129 which may be opposite the first end 127. One or both of the first and second ends 127, 129 may be open, though in other exemplary embodiments, openings may be provided at or near the first or second end 127, 129.

In the retracted position, the first end 127 of the snorkel 128 may reside at least partially within the channel 126. In the extended position, the first end 127 of the snorkel 128 may extend within the container 122. In exemplary embodiments, the snorkel 128 may be of sufficient length to extend through the entire container 122 and the spike 112 when fully inserted (e.g., when in the extended position). At a minimum, the snorkel 128 may be of sufficient length to permit the first end 127 to be elevated above a fluid level of the substance 124 in the container 122 when the snorkel 128 is in the extended position.

The snorkel 128 may comprise a fluid control device 130 at the second end 129 thereof. The fluid control device 130 may be configured to permit air to enter the snorkel 128 (and thus the container 122) while preventing the substance 124 from exiting the container 122 through the snorkel 128. Alternatively, or additional, the fluid control device 130 may be configured to prevent certain outside contaminants (e.g., dust, pollen, germs, smoke, combinations thereof, or the like) from entering the container 122 while air is ingested. The fluid control device 130 may comprise a filter, cap, valve (e.g., one- or two-way valve, check value), combinations thereof, or the like. In other exemplary embodiments, a fluid control device 130 may not be required and a finger, other appendage, or other blocking member may be placed over the second end 129, which may be otherwise open, to control fluid flow. Any number and type of fluid control devices 130 may be utilized, such as but not limited to, along the snorkel 128, at the first end 127 of the snorkel 128, combinations thereof, or the like. The first end 127 may be otherwise be open.

The delivery system 100 may comprise a protective cover 132. The protective cover 132 may include one or more adjustable length members extending between the channel 126 and the second end 129 of the snorkel 128. The protective cover 132 may be connected to the spike 112 at a first end of the cover 132. The protective cover 132 may be connected to the fluid control device 130 at a second end of the cover 132. The protective cover 132 may comprise a sheath, sleeve, combinations thereof, or the like which is capable of collapsing. The protective cover 132 may, alternatively or additionally, comprise one or more telescoping member, compressible tubing, combinations thereof, or the like. The protective cover 132 may be configured to cover a portion of the snorkel 128 extending from the channel 126. The protective cover 132 may be configured for collapsing or otherwise reducing to a size which permits the snorkel 128 to be fully extended within the channel 126, and the container 122. The protective cover 132 may be configured for expansion or otherwise increasing to a size which permits the snorkel 128 to be fully retracted from the channel 126, and thus the container 122. The protective cover 132 may permit the snorkel 128 to remain in a sterile environment despite retraction and extension. This may permit the spike 112 and/or the snorkel 128 to be reused. Alternatively, or additionally, this may permit utilization of the snorkel 128 with different size containers 122. For example, the protective cover 132 may provide a sterile environment even where a portion of the snorkel 128 is extended form the channel 126, which may be the case when relatively short containers 122 are used. For example, FIGS. 3A and 3C illustrate use with a relatively large container 122, and FIG. 3B illustrates use with a relatively small container 122.

The channel 126 may comprise one or more non-linear sections 125. The snorkel 128 may comprise sufficiently flexible materials to permit the snorkel 128 to negotiate the non-linear sections 125 of the channel 126. The snorkel 128 may comprise materials with sufficient durability and/or memory that the snorkel 128 resumes a linear orientation upon passage beyond the non-linear sections 125.

Alternatively, or additionally, the snorkel 128 may comprise one or more non-linear segments 131. The non-linear segments 131 may be configured to accommodate some or all of the non-linear sections 125 of the channel 126. For example, the snorkel 128 may be shaped to match the channel 126 when the snorkel 128 is fully inserted within the channel 126, such as when the snorkel 128 is the extended position. The non-linear nature of the sections 125 and/or segments 131 may provide the necessary fiction to temporarily secure the snorkel 128 relative to the channel 126. The snorkel 128 may comprise a sufficiently durable, memory material that normally takes a shape which include the non-linear segments 131, such as but not limited to one or more polymers.

The first end 127 of the snorkel 128 may be sharpened, blunted, or the like.

FIG. 6A and FIG. 6B illustrate another exemplary delivery system with improved fluid flow 200 (hereinafter also the "system 200"). Similar items may be numbered similarly but increased by multiples of 100 (e.g., 112 to 212). A snorkel 228 may be inserted adjacent to a spike 212. In exemplary embodiments, the container 222 may comprise a puncturable seal located on an otherwise open end thereof. The seal may be of sufficient size to accommodate at least a portion of the spike 212 and the snorkel 228. The seal may comprise a foil, rubberized material, combinations thereof, or the like. A first end 217 of the snorkel 228 in such embodiments may be blunted, though a sharpened or other type of end may be utilized. The first end 217 may be open or the opening may be located a distance from the termination of the first end 217. The snorkel 228 may be punctured through said seal adjacent to at least the portion of the said spike 212 punctured through the seal.

The snorkel 228 may comprise one or more non-linear segments 231. The non-linear segments 231 may permit a second end 229 of the snorkel 228 to extend a distance from an outer surface of the spike 212 to facilitate access to said second end 229 when said snorkel 228 is inserted into said container 222. Any shape and number of non-linear segments 231 may be utilized. The second end 229 of the snorkel 228 may be open or the opening may be located a distance from the termination of the second end 229.

One or more fluid control devices 230 may be provided at the second end 229 of the snorkel 228, along the snorkel 228, at the first end 217, combinations thereof, or the like. The fluid control devices 230 may comprise a valve, filter, combinations thereof, or the like.

The spike 212 may be vented or unvented. The spike 212 may comprise one or more pathways 219 for draining a substance 224 from said container 222. Stated another way, the spike 212 may not require a separate channel, such as channel 126, for the snorkel 228 as the snorkel 228 may be inserted into the container 222 adjacent to the spike 212. Traditional spikes (vented or non-vented) may be used with the delivery system 200, though such is not required.

The snorkel 228 may be moveable between a retracted position where said snorkel 228 is located entirely outside of said container 222, and an extended position whereby said first end 217 of said snorkel 228 extends above a fluid line 223 (actual or anticipated) of a substance 224 in said container 222 and into an air pocket 217 (actual or anticipated). The snorkel 228 and/or the seal of the container 222 may comprise one or more materials having sufficient frictional properties that said snorkel 228 is temporarily securable at said extended position, or a position between said retracted position and said extended position. Alternatively, or additionally, a securement device 233, such as but not limited to a clamp, strap, or the like, may be provided at said spike 212 for securing said snorkel 228.

Figure 7:
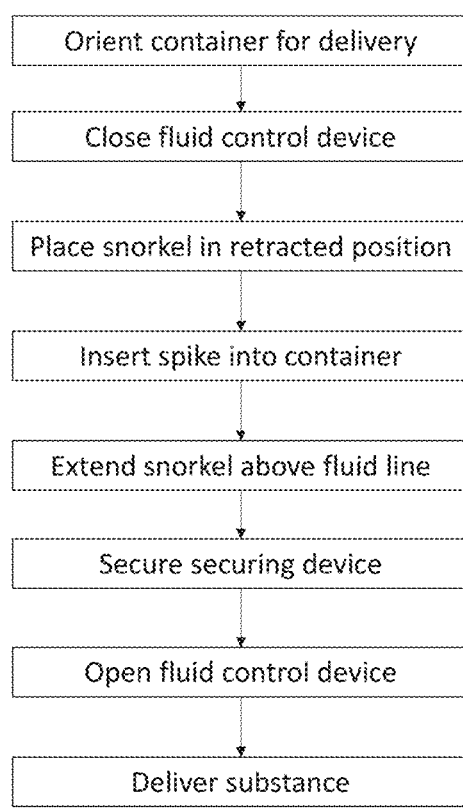
FIG. 7 is a flow chart for an exemplary method for using the delivery system of FIG. 3A-6B in accordance with the present invention.

FIG. 7 provides an exemplary flowchart for use of the system 100 and/or 200. The snorkel 128 may be provided at least partially inserted into the channel 126 of the spike 112. In other exemplary embodiments, the snorkel 128 may be provided entirely outside of the channel 126 and may be first inserted into the channel 126. In yet other exemplary embodiments, the snorkel 228 may be provided entirely outside of the spike 212 and inserted adjacent to the spike 212. The protective cover 130 may be attached to the snorkel 128 and/or the channel 126. The spike 112, 212 may be inserted into the container 122, 222. The snorkel 128, 228 may be extended such that a first end 127,227 of the snorkel 128, 228 is raised into an air pocket 117, 217 (actual or anticipated) located above a fluid line 123,223 (actual or anticipated) of the substance 124, 224 in the container 122, 222. Stated another way, the snorkel 128, 228 may be raised into the actual air pocket 117, 217 located above the actual fluid line 123, 223 if the container 122, 222 is already positioned for delivery of the substance 124, 224. Alternatively, the snorkel 128, 228 may be raised into the anticipated air pocket 117, 217 located above the anticipated fluid line 123, 223 if the container 122, 222 is not yet positioned for delivery of the substance 124, 224.

Regardless, the position of the snorkel 128, 228 within the air pocket 117, 217 above the fluid line 123, 223 may permit the introduction of ambient air into the container 122, 222 without the need for the air to bubble directly through the substance 124, 224 once the container 122, 222 is positioned for delivery of the substance 124, 224 and the delivery of the substance 124, 224 has begun, thereby permitting smooth draining of the substance 124, 224 during delivery, which may decrease or eliminate foaming and permit increased or full delivery of the substance 124, 224. Where the fluid control device 130, 230 is utilized, the fluid control device 130, 230 may be closed before the snorkel 128, 228 is raised above the fluid line 123, 223, and opened after the snorkel 128, 228 is raised above the fluid line 123, 223. In other exemplary embodiments, the fluid control device 130, 230 may be configured to automatically prevent the substance 124, 224 from traveling therebeyond, but permit ambient air to enter (e.g., one-way value). The position of the snorkel 128, 228 may be secured by the securing device 133, 233.

Figure 8A:
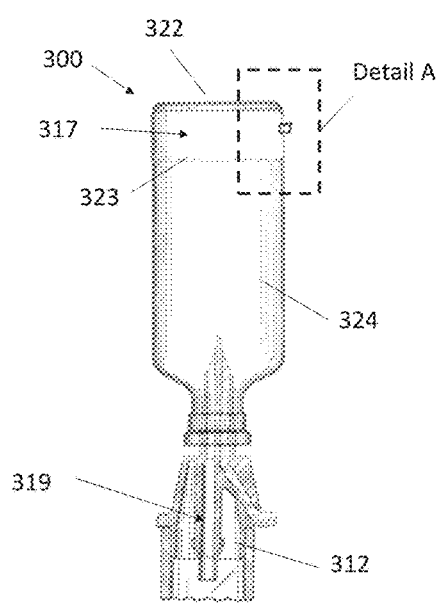
FIG. 8A is a side sectional view of another exemplary delivery system with improved fluid flow in accordance with the present invention, also illustrating detail A.
Figure 8B:
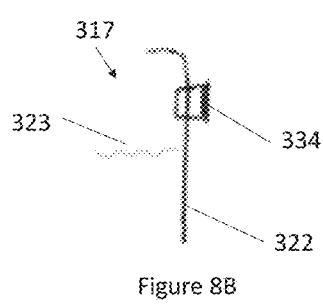
FIG. 8B is a detailed side sectional view of Detail A of FIG. 8A.
Figure 8C:
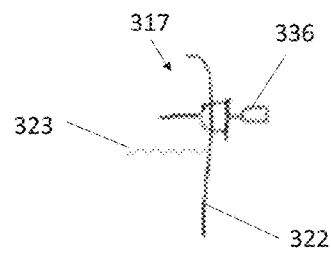
FIG. 8C is a detailed side sectional similar to FIG. 8B with an exemplary needle inserted.

FIG. 8A through FIG. 8C illustrate another exemplary delivery system with improved fluid flow 300 (hereinafter also the "system 300"). FIG. 9 illustrates an exemplary method for using the delivery system 300. Similar items may be numbered similarly but increased by multiples of 100 (e.g., 112 to 212 or 312). The delivery system 300 may comprise an airflow control device 334 provided at the container 322. The airflow control device 334 may be configured to selectively permit ambient air to enter the container 322.

The airflow control device 334 may comprise a port, cap, stopper, puncturable seal, valve (one-way, two-way, check, combinations thereof, or the like), combinations thereof, or the like. In exemplary embodiments, without limitation, the airflow control device 334 may comprise a rubber stopper. The airflow control device 334 may be positioned at a location of the container 322 within an air pocket 317 (actual or anticipated) located above a fluid line 323 (actual or anticipated) when the container 322 is positioned for administration, transfer, or other removal through a pathway 319. For example, without limitation, the airflow control device 334 may be positioned at or adjacent to a bottom surface, or at bottom portion of the container 322 such that when the spike 312 is inserted and the container 322 is oriented for delivery of the substance 324 (e.g., inverted) the airflow control device 334 is located above the fluid line 323. In this way, the air entering the container 322 does not pass through the substance 324, and thus does not create foaming. Any number of airflow control devices 334 may be utilized or the same or different type at any location on the container 322.

In exemplary embodiments, the airflow control device 334 may be configured to be remain sealed until a needle 336 or other device is inserted through the airflow control device 334 to permit air to enter the container 322. The airflow control device 334 may be configured to remain closed until certain user interaction is provided, such as but not limited to, opening a cap, removing a stopper, opening a valve, combinations thereof, or the like. Alternatively, the airflow control device 334 may be configured to remain open until certain user interaction is provided. The needle 336 may comprise a filter configured to prevent particulate of a predetermined size from entering said container 322 even when said airflow control device 334 is opened. In this way, contaminants (e.g., dust, pollen, smoke, germs, combinations thereof, or the like) may be prevented from entering the container 322 while the airflow control device 334 is opened or otherwise fully or partially unsealed.

The delivery system 300 may be used as an alternative to, or in conjunction with, the delivery system 100 and/or the delivery system 200. For example, without limitation, the snorkel 128, 228 and/or spike 112, 212 may be used in combination with the airflow control device 334, though such is not required.

Traditional spikes (vented or non-vented) may be used with the delivery system 300, though such is not required. The delivery system 300 may be used with rigid or semi-rigid containers 322, such as bottle. In other exemplary embodiments, the delivery system 300 may be used with flexible containers 322, such as bags. Even in the case of flexible containers 322, certain amounts of substance 324 may remain in the container 322, such as within creases or air pockets created during administration, transfer, or other removal. Thus, the delivery system 300 may have applicability to such flexible containers 322.

Any of the steps shown or described herein may be performed in any order, may omit one or more steps, may repeat one or more steps, or the like.

Any embodiment of the present invention may include any of the features of the other embodiments of the present invention. The exemplary embodiments herein disclosed are not intended to be exhaustive or to unnecessarily limit the scope of the invention. The exemplary embodiments were chosen and described in order to explain the principles of the present invention so that others skilled in the art may practice the invention. Having shown and described exemplary embodiments of the present invention, those skilled in the art will realize that many variations and modifications may be made to the described invention. Many of those variations and modifications will provide the same result and fall within the spirit of the claimed invention. It is the intention, therefore, to limit the invention only as indicated by the scope of the claims.

What is claimed is:

1. A method for improving a passive fluid flow during medication delivery procedures, including by minimizing foaming, said method comprising:
   puncturing a seal of a container with at least a portion of a spike, said container holding a liquid solution comprising at least one medication for infusion into a patient or pooling into a bag;
   orienting said container for said infusion or said pooling of said liquid solution;
   extending a snorkel through said seal outside of and adjacent to said spike such that a first end of said snorkel is elevated above said liquid solution when said container is oriented for said infusion or said pooling of said liquid solution and a second end of said snorkel is positioned beyond said seal to permit ingestion of ambient gasses through said snorkel and into a gaseous pocket located above said liquid solution when said container is oriented for said infusion or said pooling of said liquid solution; and
   passively draining said liquid solution through a pathway in said spike to perform said infusion or said pooling;
   wherein said snorkel is independently moveable relative to said spike;
   wherein said spike comprises a second pathway fluidly connecting the container to an ambient environment.

2. The method of claim 1 wherein:
   said snorkel comprises a first linear segment, which includes said first end, and a second linear segment, which includes said second end and extends directly from the first linear segment;
   at least a portion of said first linear segment extends through the seal and within said container until said first end thereof reaches said gaseous pocket;
   said second linear segment remains outside of said container while said liquid solution is drained from said container; and
   an acute angle is formed between a longitudinal axis of said first linear segment and a longitudinal axis of the second linear segment.

3. The method of claim 2 further comprising:
   securing, by way of a securement device, said snorkel to said spike while draining said liquid solution from said container.

4. The method of claim 3 wherein.

5. The method of claim 1 wherein:
   no liquid solution is drained through said snorkel during said infusion or said pooling.

6. The method of claim 1 further comprising:
   opening a fluid control device provided at said snorkel before draining said liquid solution from said container to permit the ingestion of the ambient gasses, wherein said fluid control device is located at said second end of said snorkel and comprises a valve and a filter.

7. The method of claim 1 wherein:

orienting said container for said infusion or said transfer of said liquid solution comprises orienting said container vertically such that said seal faces a ground surface;

said container is a rigid or semi-rigid bottle comprising glass or a polymer; and the snorkel is separable from, and independent of, the spike.

8. The method of claim 1 wherein:

said spike is part of an IV set comprising a drip chamber and an IV line; and said drip chamber is connected to said spike and said IV line at least during the step of passively draining said liquid solution through said pathway in said spike to perform said infusion or said pooling.

9. The method of claim 1 wherein:

said first end of said snorkel is located above said second end of said snorkel when said container is oriented for said infusion or said pooling.

10. A method for improving a passive fluid flow during medication delivery procedures, including by minimizing foaming, said method comprising:

providing a container holding a liquid solution comprising at least one medication for infusion into a patient or pooling into a bag;

inserting a spike of an intravenous (IV) set through a seal of the container;

inserting a snorkel, which is separate from and independently moveable relative to the spike, from outside of the container through the seal outside of and alongside said spike and extending the snorkel by sliding movement through the container until a first end of said snorkel is located at a position whereby the first end is elevated above said liquid solution when said container is oriented for said infusion or said pooling and a second end of said snorkel remains outside of the container;

orienting said container for said infusion or said pooling; and while the container remains oriented for said infusion or said pooling, passively draining said liquid solution through a pathway in said spike into a drip chamber connected to said spike and an IV line of said IV set to perform said infusion or said pooling while simultaneously ingesting ambient gasses through said snorkel and into a gaseous pocket located above said liquid solution;

wherein the spike comprises a second pathway fluidly connecting the container to an ambient environment.

11. The method of claim 10 further comprising:

clamping a clamp about a portion of said snorkel located beyond said seal to secure said snorkel relative to said spike.

12. The method of claim 10 wherein:

said first end of said snorkel is located above said second end of said snorkel when said container is oriented for said infusion or said pooling.

\* \* \* \* \*